US008119857B2

(12) United States Patent
Harris et al.

(10) Patent No.: US 8,119,857 B2
(45) Date of Patent: Feb. 21, 2012

(54) POLYPEPTIDES HAVING ENDOGLUCANASE ACTIVITY AND POLYNUCLEOTIDES ENCODING SAME

(75) Inventors: Paul Harris, Carnation, WA (US); Alfredo Lopez de Leon, Davis, CA (US); Micheal Rey, Davis, CA (US); Hanshu Ding, Davis, CA (US); Elena Vlasenko, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 12/892,614

(22) Filed: Sep. 28, 2010

(65) Prior Publication Data

US 2011/0014707 A1    Jan. 20, 2011

Related U.S. Application Data

(62) Division of application No. 11/413,022, filed on Apr. 27, 2006, now Pat. No. 7,824,884.

(60) Provisional application No. 60/675,601, filed on Apr. 27, 2005.

(51) Int. Cl.
*C12N 15/31* (2006.01)
*C12N 15/82* (2006.01)
*C12N 15/10* (2006.01)
*C12N 15/52* (2006.01)
*A01H 5/00* (2006.01)

(52) U.S. Cl. ........ 800/288; 800/284; 800/295; 800/278; 435/320.1; 435/468; 536/23.1; 536/23.2; 536/23.7

(58) Field of Classification Search ........................ None
See application file for complete search history.

(56) References Cited

U.S. PATENT DOCUMENTS

| 5,393,670 | A | 2/1995 | Knowles et al. | |
|---|---|---|---|---|
| 6,500,658 | B1 | 12/2002 | Wu et al. | |
| 2010/0299788 | A1* | 11/2010 | Harris et al. | 800/295 |
| 2010/0299789 | A1* | 11/2010 | Harris et al. | 800/298 |
| 2010/0304434 | A1* | 12/2010 | Harris et al. | 435/69.1 |
| 2010/0306881 | A1* | 12/2010 | Harris et al. | 800/298 |

FOREIGN PATENT DOCUMENTS

WO    WO 97-14804    4/1997

OTHER PUBLICATIONS

Penttila et al, Homology between cellulase genes of *Trichoderma reesei*: complete nucleotide sequence of the endoglucanase I gene, Gene, vol. 45, 1986, pp. 253-263.
Leinonen T., Opposition against EP 1 877 551 B1, Experimental Report, 2010.
Schulein et al., Characterization of Fungal Cellulases for Fiber Modification, Enzyme Appl in Fiber Processing, 1998, pp. 66-74.
Penttila et al., Expression of Two *Trichoderma reesei* Endoglucanases in the Yeast *Saccharomyces cerevisiae*, Yeast, 1987, vol. 3, pp. 175-185.
Haakana et al., Cloning of cellulase genes from *Melanocarpus albomyces* and their efficient expression in *Trichoderma reesei*, Enzyme and Microbial Technology 34 (2004) 159-167.
Kitamoto et al., Molecular cloning, purification and characterization of two endo-1,4-beta-glucanases from Aspergillus oryzae KBN616, Appl Microbiol Biotechnol (1996) 46: 538-544.
Breuil et al, Production and localization of cellulases and B-glucosidase from the thermophilic fungus *Thielavia terrestris*, Biotechnology Letters, vol. 8, No. 9, 1986, pp. 673-676.
Gilbert et al., Characterization of the Enzymes present in the cellulase system of *Thielavia terrestris* 255B, Bioresource Technology, v. 39, 1992, pp. 147-154.
Kvesitade et al., Isolation and properties of a thermostable endoglucanase from a thermophilic mutant strain of *Thielavia terrestris*, Applied Biochemistry and Biotechnology, vol. 50, 1995, pp. 137-143.
Arsdell et al., Cloning, characterization, and expression in *Saccharomyces cerevisiae* of endoglucanase I from *Trichoderma reesei*, Bio/Technology, 1987, vol. 5, No. 1, pp. 60-64.
XP002405164, EBI, EM PRO: TREGI, Database accession No. M15665, 1986.
Kleywegt et al., The crystal structure of the catalytic core domain of endoglucanase I from *Trichoderma reesei* at 3.6 A resolution, and a comparison with related enzymes, J. Mol. Biol., 1997, Vo. 272, pp. 383-397.
Gilkes et al., Domains in microbial beta-1, 4-glycanases: sequence conservation, function, and enzyme families, Microbiological Reviews, Jun. 1991, vol. 55, No. 2, pp. 303-315.
Henrissat B, A classification of glycosyl hydrolases based on amino acid sequence similarities, Biochem, J., 1991, vol. 280, pp. 309-316.
Kataeva et al., Properties and Mutation Analysis of the CelK Cellulose-Binding Domain from the *Clostridium thermocellum* Cellulosome, J Bacteriol, (1998) 183: 1552-1559.
Van Arsdell et al., Cloning, characterization, and expression in *Saccharomyces cerevisiae* of endoglucanase I from *Trichoderma reesei*, Biotechnology, (1987) 5: 60-64.

\* cited by examiner

*Primary Examiner* — Brent T Page
(74) *Attorney, Agent, or Firm* — Robert L. Starnes; Eric J. Fechter

(57) ABSTRACT

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

25 Claims, 9 Drawing Sheets

```
      M   T   L   R   L   P   V   I   S   L   L   A   S   L   A   A   G
  1   ATGACCCTACGGCTCCCTGTCATCAGCCTGCTGGCCTCGCTGGCAGCAGGC
      A   V   V   V   P   R   A   E   F   H   P   P   L   P   T   W   K
 52   GCCGTCGTCGTCCCACGGGCGGAGTTTCACCCCCCTCTCCCGACTTGGAAA
      C   T   T   S   G   G   C   V   Q   Q   N   T   S   V   V   L   D
103   TGCACGACCTCCGGGGGCTGCGTGCAGCAGAACACCAGCGTCGTCCTGGAC
      R   D   S   K   Y   A   A   H   S   A   G   S   R   T   E   S   D
154   CGTGACTCGAAGTACGCCGCACACAGCGCCGGCTCGCGGACGGAATCGGAT
      Y   A   A   M   G   V   S   T   S   G   N   A   V   T   L   Y   H
205   TACGCGGCAATGGGAGTGTCCACTTCGGGCAATGCCGTGACGCTGTACCAC
      Y   V   K   T   N   G   T   L   V   P   A   S   P   R   I   Y   L
256   TACGTCAAGACCAACGGCACCCTCGTCCCCGCTTCGCCGCGCATCTACCTC
      L   G   A   D   G   K   Y   V   L   M   D   L   L   N   Q   E   L
307   CTGGGCGCGGACGGCAAGTACGTGCTTATGGACCTCCTCAACCAGGAGCTG
      S   V   D   V   D   F   S   A   L   P   C   G   E   N   G   A   F
358   TCGGTGGACGTCGACTTCTCGGCGCTGCCGTGCGGCGAGAACGGGGCCTTC
      Y   L   S   E   M   A   A   D   G   R   G   D   A   G   A   G   D
409   TACCTGTCCGAGATGGCGGCGGACGGGCGGGGCGACGCGGGGGCGGGCGAC
      G   Y   C   D   A   Q   C   Q   G   Y   C   C   N   E   M   D   I
460   GGGTACTGCGACGCGCAGTGCCAGGGCTACTGCTGCAACGAGATGGACATC
      L   E   A   N   S   M   A   T   A   M   T   P   H   C   K   G
511   CTCGAGGCCAACTCGATGGCGACGGCCATGACGCCGCACCCGTGCAAGGGC
      N   N   C   D   R   S   G   C   G   Y   N   P   Y   A   S   G   Q
562   AACAACTGCGACCGCAGCGGCTGCGGCTACAACCCGTACGCCAGCGGCCAG
      R   G   F   Y   G   P   G   K   T   V   D   T   S   K   P   F   T
613   CGCGGCTTCTACGGGCCCGGCAAGACGGTCGACACGAGCAAGCCCTTCACC
      V   V   T   Q   F   A   A   S   G   G   K   L   T   Q   I   T   R
664   GTCGTCACGCAGTTCGCCGCCAGCGGCGGCAAGCTGACCCAGATCACCCGC
      K   Y   I   Q   N   G   R   E   I   G   G   G   G   T   I   S   S
715   AAGTACATCCAGAACGGCCGGGAGATCGGCGGCGGCGGCACCATCTCCAGC
      C   G   S   E   S   S   T   G   G   L   T   G   M   G   E   A   L
766   TGCGGCTCCGAGTCTTCGACGGGCGGCCTGACCGGCATGGGCGAGGCGCTG
      G   R   G   M   V   L   A   M   S   I   W   N   D   A   A   Q   E
817   GGGCGCGGAATGGTGCTGGCCATGAGCATCTGGAACGACGCGGCCCAGGAG
      M   A   W   L   D   A   G   N   N   G   P   C   A   S   G   Q   G
```

Fig. 1A

```
868  ATGGCATGGCTCGATGCCGGCAACAACGGCCCTTGCGCCAGTGGCCAGGGC
      S   P   S   V   I   Q   S   Q   H   P   D   T   H   V   V   F   S
919  AGCCCGTCCGTCATTCAGTCGCAGCATCCCGACACCCACGTCGTCTTCTCC
      N   I   R   W   G   D   I   G   S   T   T   K   N   *
970  AACATCAGGTGGGGCGACATCGGGTCTACCACGAAGAACTAG
```

POLYPEPTIDES HAVING ENDOGLUCANASE ACTIVITY AND POLYNUCLEOTIDES ENCODING SAME

CROSS-REFERENCE TO RELATED APPLICATION

This application is a divisional application of U.S. application Ser. No. 11/413,022 filed Apr. 27, 2006, now U.S. Pat. No. 7,824,884, which claims the benefit of U.S. Provisional Application No. 60/675,601, filed Apr. 27, 2005, which applications are incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiohydrolase I is a 1,4-D-glucan cellobiohydrolase (E.C. 3.2.1.91) activity which catalyzes the hydrolysis of 1,4-beta-D-glucosidic linkages in cellulose, cellotetriose, or any beta-1,4-linked glucose containing polymer, releasing cellobiose from the reducing ends of the chain. Cellobiohydrolase II is a 1,4-D-glucan cellobiohydrolase (E.C. 3.2.1.91) activity which catalyzes the hydrolysis of 1,4-beta-D-glucosidic linkages in cellulose, cellotetriose, or any beta-1,4-linked glucose containing polymer, releasing cellobiose from the non-reducing ends of the chain. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

Kvesitadaze et al., 1995, *Applied Biochemistry and Biotechnology* 50: 137-143, describe the isolation and properties of a thermostable endoglucanase from a thermophilic mutant strain of *Thielavia terrestris*. Gilbert et al., 1992, *Bioresource Technology* 39: 147-154, describe the characterization of the enzymes present in the cellulose system of *Thielavia terrestris* 255B. Breuil et al., 1986, *Biotechnology Letters* 8: 673-676, describe production and localization of cellulases and beta-glucosidases from *Thielavia terrestris* strains C464 and NRRL 8126.

It would be an advantage in the art to identify new endoglucanases having improved properties, such as improved hydrolysis rates, better thermal stability, reduced adsorption to lignin, and the ability to hydrolyze non-cellulosic components of biomass, such as hemicellulose, in addition to hydrolyzing cellulose. Endoglucanases with a broad range of side activities on hemicellulose can be especially beneficial for improving the overall hydrolysis yield of complex, hemicellulose-rich biomass substrates.

It is an object of the present invention to provide improved polypeptides having endoglucanase activity and polynucleotides encoding the polypeptides.

SUMMARY OF THE INVENTION

The present invention relates to isolated polypeptides having endoglucanase activity selected from the group consisting of:

(a) a polypeptide comprising an amino acid sequence which has at least 60% identity with the mature polypeptide coding sequence of SEQ ID NO: 2;

(b) a polypeptide which is encoded by a nucleotide sequence which hybridizes under at least medium stringency conditions with (i) the mature polypeptide coding sequence of SEQ ID NO: 1, (ii) the genomic DNA sequence comprising the mature polypeptide coding sequence of SEQ ID NO: 1, or (iii) a complementary strand of (i) or (ii); and (c) a variant comprising a conservative substitution, deletion, and/or insertion of one or more amino acids of the mature polypeptide of SEQ ID NO: 2.

The present invention also relates to isolated polynucleotides encoding polypeptides having endoglucanase activity, selected from the group consisting of:

(a) a polynucleotide encoding a polypeptide comprising an amino acid sequence which has at least 60% identity with the mature polypeptide of SEQ ID NO: 2;

(b) a polynucleotide having at least 60% identity with the mature polypeptide coding sequence of SEQ ID NO: 1; and (c) a polynucleotide which hybridizes under at least low stringency conditions with (i) the mature polypeptide coding sequence of SEQ ID NO: 1, (ii) the genomic DNA sequence comprising the mature polypeptide coding sequence of SEQ ID NO: 1, or (iii) a complementary strand of (i) or (ii).

In a preferred aspect, the mature polypeptide is amino acids 18 to 336 of SEQ ID NO: 2. In another preferred aspect, the mature polypeptide coding sequence is nucleotides 52 to 1008 of SEQ ID NO: 1.

The present invention also relates to nucleic acid constructs, recombinant expression vectors, and recombinant host cells comprising the polynucleotides.

The present invention also relates to methods for producing such a polypeptide having endoglucanase activity comprising: (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the polypeptides having endoglucanase activity in detergents and in the conversion of cellulose to glucose.

The present invention further relates to nucleic acid constructs comprising a gene encoding a protein, wherein the gene is operably linked to a nucleotide sequence encoding a signal peptide comprising or consisting of amino acids 1 to 17 of SEQ ID NO: 2, wherein the gene is foreign to the nucleotide sequence.

BRIEF DESCRIPTION OF THE FIGURES

FIGS. 1A and 1B show the cDNA sequence and the deduced amino acid sequence of a *Thielavia terrestris* NRRL 8126 endoglucanase (CEL7F) (SEQ ID NOs: 1 and 2, respectively).

DEFINITIONS

Figure 2:
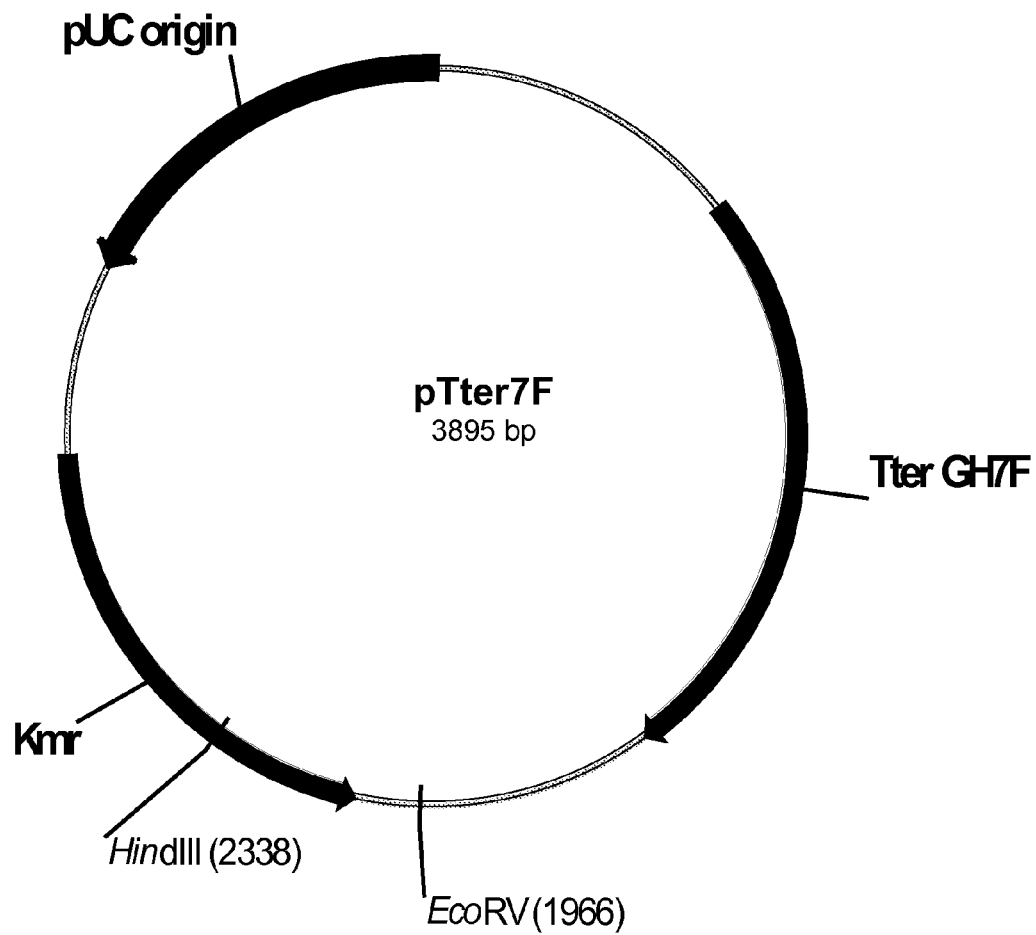
FIG. 2 shows a restriction map of pTter7F.

Endoglucanase activity: The term "endoglucanase activity" is defined herein as an endo-1,4-beta-D-glucan 4-glucanohydrolase (E.C. No. 3.2.1.4) which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268. One unit of endoglucanase activity is defined as 1.0 μmole of reducing sugars produced per minute at 50° C., pH 4.8.

In a preferred aspect, the polypeptides of the present invention having endoglucanase activity further have enzyme activity toward one or more substrates selected from the group consisting of xylan, xyloglucan, arabinoxylan, galactan, galactomannan, dextran, and chitin. The activity of the polypeptides having endoglucanase activity on these polysaccharide substrates is determined as the relative amount of dye released from different AZCL-dyed substrates after incubating the substrates (5 g per liter) with a polypeptide having endoglucanase activity of the present invention (1 mg protein per g of substrate) for 1 and 92 hours without stirring at pH 5.0 (50 mM sodium acetate) and 50° C. The release of dye was determined by measuring the absorbance at 590 nm.

In a more preferred aspect, the polypeptides of the present invention having endoglucanase activity further have enzyme activity toward xylan. In another more preferred aspect, the polypeptides of the present invention having endoglucanase activity further have enzyme activity toward xyloglucan. In another more preferred aspect, the polypeptides of the present invention having endoglucanase activity further have enzyme activity toward arabinoxylan. In another more preferred aspect, the polypeptides of the present invention having endoglucanase activity further have enzyme activity toward galactan. In another more preferred aspect, the polypeptides of the present invention having endoglucanase activity further have enzyme activity toward galactomannan. In another more preferred aspect, the polypeptides of the present invention having endoglucanase activity further have enzyme activity toward dextran. In another more preferred aspect, the polypeptides of the present invention having endoglucanase activity further have enzyme activity toward chitin. In another more preferred aspect, the polypeptides of the present invention having endoglucanase activity further have enzyme activity toward xylan, xyloglucan, arabinoxylan, galactan, galactomannan, dextran, and chitin.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the endoglucanase activity of the polypeptide consisting of the amino acid sequence shown as amino acids 18 to 336 of SEQ ID NO: 2.

Family 7 glycoside hydrolase or Family GH7: The term "Family 7 glycoside hydrolase" or "Family GH7" or "CEL7F" is defined herein as a polypeptide falling into the glycoside hydrolase Family 7 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Mature polypeptide: The term "mature polypeptide" is defined herein as a polypeptide having endoglucanase activity that is in its final form following translation and any post-translational modifications, such as N-terminal processing, C-terminal truncation, glycosylation, etc.

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide fragment: The term "polypeptide fragment" is defined herein as a polypeptide having one or more amino acids deleted from the amino and/or carboxyl terminus of SEQ ID NO: 2 or a homologous sequence thereof, wherein the fragment has endoglucanase activity. Preferably, a fragment contains at least 270 amino acid residues, more preferably at least 285 amino acid residues, and most preferably at least 300 amino acid residues, e.g., amino acids 18 to 336 of SEQ ID NO: 2.

Subsequence: The term "subsequence" is defined herein as a nucleotide sequence having one or more nucleotides deleted from the 5' and/or 3' end of SEQ ID NO: 1 or a homologous sequence thereof, wherein the subsequence encodes a polypeptide fragment having endoglucanase activity. Preferably, a subsequence contains at least 810 nucleotides, more preferably at least 855 nucleotides, and most preferably at least 900 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Mature polypeptide coding sequence: The term "mature polypeptide coding sequence" is defined herein as a nucleotide sequence that encodes a mature polypeptide having endoglucanase activity.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2 or a homologous sequence thereof as well as genetic manipulation of the DNA encoding that polypeptide. The modification can be substitutions, deletions and/or insertions of one or more amino acids as well as replacements of one or more amino acid side chains.

Artificial variant: When used herein, the term "artificial variant" means a polypeptide having endoglucanase activity produced by an organism expressing a modified nucleotide sequence of SEQ ID NO: 1 or a homologous sequence thereof, or the mature coding region thereof. The modified nucleotide sequence is obtained through human intervention by modification of the nucleotide sequence disclosed in SEQ ID NO: 1 or a homologous sequence thereof, or the mature coding region thereof.

DETAILED DESCRIPTION OF THE INVENTION

Polypeptides Having Endoglucanase Activity

In a first aspect, the present invention relates to isolated polypeptides comprising an amino acid sequence which has a degree of identity to the mature polypeptide of SEQ ID NO: 2 of at least 60%, preferably at least 65%, more preferably at least 70%, more preferably at least 75%, more preferably at least 80%, more preferably at least 85%, even more preferably at least 90%, most preferably at least 95%, and even most preferably at least 97%, 98%, or 99%, which have endoglucanase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof that has endoglucanase activity. In a preferred aspect, a polypeptide comprises the amino acid sequence of SEQ ID NO: 2. In another preferred aspect, a polypeptide comprises the mature polypeptide of SEQ ID NO: 2. In another preferred aspect, a polypeptide comprises amino acids 18 to 336 of SEQ ID NO: 2, or an allelic variant thereof; or a fragment thereof that has endoglucanase activity. In another preferred aspect, a polypeptide comprises amino acids 18 to 336 of SEQ ID NO: 2. In another preferred aspect, a polypeptide consists of the amino acid sequence of SEQ ID NO: 2 or an allelic variant thereof; or a fragment thereof that has endoglucanase activity. In another preferred aspect, a polypeptide consists of the amino acid sequence of SEQ ID NO: 2. In another preferred aspect, a polypeptide consists of the mature polypeptide of SEQ ID NO: 2. In another preferred aspect, a polypeptide consists of amino acids 18 to 336 of SEQ ID NO: 2 or an allelic variant thereof; or a fragment thereof that has endoglucanase activity. In another preferred aspect, a polypeptide consists of amino acids 18 to 336 of SEQ ID NO: 2.

In a second aspect, the present invention relates to isolated polypeptides having endoglucanase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, (iii) a subsequence of (i) or (ii), or (iv) a complementary strand of (i), (ii), or (iii) (J. Sambrook, E. F. Fritsch, and T. Maniatis, 1989, Molecular Cloning, A Laboratory Manual, 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has endoglucanase activity. In a preferred aspect, the mature polypeptide coding sequence is nucleotides 52 to 1008 of SEQ ID NO: 1.

The nucleotide sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having endoglucanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having endoglucanase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, the genomic DNA sequence comprising SEQ ID NO: 1, its complementary strand, or a subsequence thereof, under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 52 to 1008 of SEQ ID NO: 1. In another preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the mature polypeptide coding sequence of SEQ ID NO: 1. In another preferred aspect, the nucleic acid probe is the polynucleotide sequence contained in plasmid pTter7F which is contained in *E. coli* NRRL B-30837, wherein the polynucleotide sequence thereof encodes a polypeptide having lipase activity. In another preferred aspect, the nucleic acid probe is the mature polypeptide coding sequence contained in plasmid pTter7F which is contained in *E. coli* NRRL B-30837.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to artificial variants comprising a conservative substitution, deletion, and/or insertion of one or more amino acids of SEQ ID NO: 2 or a homologous sequence thereof; or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., endoglucanase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 18 to 336 of SEQ ID NO: 2, is 10, preferably 9, more preferably 8, more preferably 7, more preferably at most 6, more preferably 5, more preferably 4, even more preferably 3, most preferably 2, and even most preferably 1.

Sources of Polypeptides Having Endoglucanase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide having endoglucanase activity; or a *Streptomyces* polypeptide having endoglucanase activity, e.g., a *Streptomyces lividans* or *Streptomyces murinus* polypeptide having endoglucanase activity; or a gram negative bacterial polypeptide, e.g., an *E. coli* or a *Pseudomonas* sp. polypeptide having endoglucanase activity.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide having endoglucanase activity; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide having endoglucanase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having endoglucanase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide having endoglucanase activity.

In another preferred aspect, the polypeptide is a *Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Thielavia terricola, Thielavia thermophila, Thielavia variospora*, or *Thielavia wareingii* polypeptide having endoglucanase activity.

In a more preferred aspect, the polypeptide is a *Thielavia terrestris* polypeptide having endoglucanase activity, and most preferably a *Thielavia terrestris* NRRL 8126 polypeptide having endoglucanase activity, e.g., the polypeptide of SEQ ID NO: 2 or the mature polypeptide thereof.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides comprising or consisting of a nucleotide sequence which encode a polypeptide of the present invention having endoglucanase activity.

In a preferred aspect, the nucleotide sequence comprises or consists of SEQ ID NO: 1. In another more preferred aspect, the nucleotide sequence comprises or consists of the sequence contained in plasmid pTter7F which is contained in *E. coli* NRRL B-30837. In another preferred aspect, the nucleotide sequence comprises or consists of the mature polypeptide coding region of SEQ ID NO: 1. In another preferred aspect, the nucleotide sequence comprises or consists of nucleotides 52 to 1008 of SEQ ID NO: 1. In another more preferred aspect, the nucleotide sequence comprises or consists of the mature polypeptide coding region contained in plasmid pTter7F which is contained in *E. coli* NRRL B-30837. The present invention also encompasses nucleotide sequences which encode a polypeptide comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 which encode fragments of SEQ ID NO: 2 that have endoglucanase activity.

The present invention also relates to mutant polynucleotides comprising at least one mutation in the mature polypeptide coding sequence of SEQ ID NO: 1, in which the mutant nucleotide sequence encodes the mature polypeptide of SEQ ID NO: 2. In a preferred aspect, the mature polypeptide is amino acids 18 to 336 of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to polynucleotides comprising nucleotide sequences which have a degree of identity to the mature polypeptide coding sequence of SEQ ID NO: 1 of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 52 to 1008 of SEQ ID NO: 1.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for endoglucanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the genomic DNA sequence comprising the mature polypeptide coding sequence of SEQ ID NO: 1, or (iii) a complementary strand of (i) or (ii); or allelic variants and subsequences thereof (Sambrook et al., 1989, supra), as defined herein. In a preferred aspect, the mature polypeptide coding sequence is nucleotides 52 to 1008 of SEQ ID NO: 1.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the genomic DNA sequence comprising the mature polypeptide coding sequence of SEQ ID NO: 1, or (iii) a complementary strand of (i) or (ii); and (b) isolating the hybridizing polynucleotide, which encodes a polypeptide having endoglucanase activity. In a preferred aspect, the mature polypeptide coding sequence is nucleotides 52 to 1008 of SEQ ID NO: 1.

Nucleic Acid Constructs

The present invention also relates to nucleic acid constructs comprising an isolated polynucleotide of the present invention operably linked to one or more control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide is amino acids 1 to 17 of SEQ ID NO: 2. In another preferred aspect, the signal peptide coding region is nucleotides 1 to 51 of SEQ ID NO: 1 which encode amino acids 1 to 17 of SEQ ID NO: 2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizen, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*,

*Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Thielavia terricola, Thielavia thermophila, Thielavia variospora, Thielavia wareingii, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising: (a) cultivating a cell, which in its wild-type form is capable of producing the polypeptide, under conditions conducive for production of the polypeptide; and (b) recovering the polypeptide. In a preferred aspect, the cell is of the genus *Thielavia*. In a more preferred aspect, the cell is *Thielavia terrestris*. In a most preferred aspect, the cell is *Thielavia terrestris* NRRL 8126.

The present invention also relates to methods for producing a polypeptide of the present invention, comprising: (a) cultivating a host cell under conditions conducive for production of the polypeptide; and (b) recovering the polypeptide.

The present invention also relates to methods for producing a polypeptide of the present invention, comprising: (a) cultivating a host cell under conditions conducive for production of the polypeptide, wherein the host cell comprises a mutant nucleotide sequence comprising at least one mutation in the mature polypeptide coding sequence of SEQ ID NO: 1, wherein the mutant nucleotide sequence encodes a polypeptide which consists of the mature polypeptide of SEQ ID NO: 2, and (b) recovering the polypeptide. In a preferred aspect, the mature polypeptide is amino acids 18 to 336 of SEQ ID NO: 2.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to a transgenic plant, plant part, or plant cell which has been transformed with a nucleotide sequence encoding a polypeptide having endoglucanase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, Cell 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising: (a) cultivating a transgenic plant or a plant cell comprising a polynucleotide encoding a polypeptide having endoglucanase activity of the present invention under conditions conducive for production of the polypeptide; and (b) recovering the polypeptide.

Removal or Reduction of Endoglucanase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising: (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of endoglucanase activity by fermentation of a cell which produces both a polypeptide of the present invention as well as the protein product of interest by adding an effective amount of an agent capable of inhibiting endoglucanase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of endoglucanase activity by cultivating the cell under conditions permitting the expression of the product, subjecting the resultant culture broth to a combined pH and temperature treatment so as to reduce the endoglucanase activity substantially, and recovering the product from the culture broth. Alternatively, the combined pH and temperature treatment may be performed on an enzyme preparation recovered from the culture broth. The combined pH and temperature treatment may optionally be used in combination with a treatment with an endoglucanase inhibitor.

In accordance with this aspect of the invention, it is possible to remove at least 60%, preferably at least 75%, more preferably at least 85%, still more preferably at least 95%, and most preferably at least 99% of the endoglucanase activity. Complete removal of endoglucanase activity may be obtained by use of this method.

The combined pH and temperature treatment is preferably carried out at a pH in the range of 2-3 or 10-11 and a temperature in the range of at least 75-85° C. for a sufficient period of time to attain the desired effect, where typically, 1 to 3 hours is sufficient.

The methods used for cultivation and purification of the product of interest may be performed by methods known in the art.

The methods of the present invention for producing an essentially endoglucanase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The endoglucanase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from endoglucanase activity which is produced by a method of the present invention.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having endoglucanase activity, or compositions thereof.

Degradation of Biomass to Monosaccharides, Disaccharides, and Polysaccharides

The polypeptides having endoglucanase activity, and host cells of the present invention, may be used in the production of monosaccharides, disaccharides, and polysaccharides as chemical or fermentation feedstocks from biomass for the production of ethanol, plastics, or other products or intermediates. The polypeptides having endoglucanase activity may be in the form of a crude fermentation broth with or without the cells removed or in the form of a semi-purified or purified enzyme preparation. Alternatively, a host cell of the present invention may be used as a source of the polypeptide having endoglucanase activity in a fermentation process with the biomass.

Biomass can include, but is not limited to, wood resources, municipal solid waste, wastepaper, and crop residues (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, *Recent Progress in Bioconversion of Lignocellulosics*, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of glycohydrolases are used to breakdown cellulosic biomass:

(1) The "endo-1,4-beta-glucanases" or 1,4-beta-D-glucan-4-glucanohydrolases (EC 3.2.1.4), which act randomly on soluble and insoluble 1,4-beta-glucan substrates.

(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.

(3) The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically resulting in efficient decrystallization and hydrolysis of native cellulose from biomass to yield reducing sugars.

The polypeptides having endoglucanase activity of the present invention may be used in conjunction with the above-noted enzymes to further degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

Ethanol can be produced by enzymatic degradation of biomass and conversion of the released saccharides to ethanol. This kind of ethanol is often referred to as bioethanol or biofuel. It can be used as a fuel additive or extender in blends of from less than 1% and up to 100% (a fuel substitute).

Detergent Compositions

The polypeptides having endoglucanase activity of the present invention may be added to and thus become a component of a detergent composition.

The detergent composition of the present invention may be, for example, formulated as a hand or machine laundry detergent composition including a laundry additive composition suitable for pre-treatment of stained fabrics and a rinse added fabric softener composition, or formulated as a detergent composition for use in general household hard surface cleaning operations, or formulated for hand or machine dishwashing operations.

In a specific aspect, the present invention provides a detergent additive comprising the polypeptides having endoglucanase activity of the present invention. The detergent additive as well as the detergent composition may comprise one or more other enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the enzymatic components should be compatible with the selected detergent, (i.e., pH-optimum, compatibility with other enzymatic and non-enzymatic ingredients, etc.), and the enzymatic components should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g., from H. lanuginosa (T. lanuginosus) as described in EP 258 068 and EP 305 216 or from H. insolens as described in WO 96/13580, a Pseudomonas lipase, e.g., from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g., from B. subtilis (Dartois et al., 1993, Biochemica et Biophysica Acta, 1131, 253-360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipases include Lipolase™, Lipex™, and Lipolase Ultra™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g., a special strain of Bacillus licheniformis, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, or Trichoderma e.g., the fungal cellulases produced from Humicola insolens, Myceliophthora thermophila and Fusarium oxysporum disclosed in U.S. Pat. No. 4,435,307, U.S. Pat. No. 5,648,263, U.S. Pat. No. 5,691,178, U.S. Pat. No. 5,776,757, and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluclast®, Celluzyme™, and Carezyme™ (Novozymes A/S), Clazinase™, and Puradax HA™ (Genencor International Inc.), and KAC-500(B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257.

Commercially available peroxidases include Guardzyme™ (Novozymes A/S).

The enzymatic component(s) may be included in a detergent composition by adding separate additives containing one or more enzymes, or by adding a combined additive comprising all of these enzymes. A detergent additive of the present invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the present invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system that may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzymatic component(s) of the detergent composition of the present invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzymatic component, in particular the polypeptides having endoglucanase activity of the present invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The polypeptides having endoglucanase activity of the present invention may additionally be incorporated in the detergent formulations disclosed in WO 97/07202 which is hereby incorporated as reference.

Signal Peptide

The present invention also relates to nucleic acid constructs comprising a gene encoding a protein operably linked to a nucleotide sequence encoding a signal peptide comprising or consisting of amino acids 1 to 17 of SEQ ID NO: 2, which allows secretion of the protein into a culture medium, wherein the gene is foreign to the nucleotide sequence.

In a preferred aspect, the nucleotide sequence comprises nucleotides 1 to 51 of SEQ ID NO: 1. In another preferred aspect, the nucleotide sequence consists of nucleotides 1 to 51 of SEQ ID NO: 1.

The present invention also relates to recombinant expression vectors and recombinant host cells comprising such nucleic acid constructs.

The present invention also relates to methods for producing a protein comprising: (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

SDS-PAGE gels, loading buffer, and running buffer were obtained from Invitrogen/Novex (Carlsbad, Calif.). Sequencing grade modified trypsin was from Princeton Separations (Aldelphia, N.J.). BioSafe Commassie Blue G250 protein stains were obtained from BioRad Laboratories (Hercules, Calif.).

Strains

*Aspergillus oryzae* JaL250 strain (WO 99/61651) was used for expression of a *Thielavia terrestris* polypeptide having endoglucanase activity. *Thielavia terrestris* NRRL strain 8126 was used as the source of a gene for a Family 7F polypeptide having endoglucanase activity.

Media

PDA plates were composed per liter of 39 grams of potato dextrose agar.

NNCYP medium was composed per liter of 5.0 g of $NH_4NO_3$, 0.5 g of $MgSO_4.7H_2O$, 0.3 g of $CaCl_2$, 2.5 g of citric acid, 1.0 g of Bacto Peptone, 5.0 g of yeast extract, 1 ml of COVE trace metals, and sufficient $K_2HPO_4$ to achieve a final pH of approximately 5.4.

NNCYPmod medium was composed per liter of 1.0 g of NaCl, 5.0 g of $NH_4NO_3$, 0.2 g of $MgSO_4.7H_2O$, 0.2 g of $CaCl_2$, 2.0 g of citric acid, 1.0 g of Bacto Peptone, 5.0 g of yeast extract, 1 ml of COVE trace metals solution, and sufficient $K_2HPO_4$ to achieve the final pH of approximately 5.4.

Cove trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

LB plates were composed per liter of 10 g of tryptone, 5 g of yeast extract, 5 g of sodium chloride, and 15 g of Bacto Agar.

MDU2BP medium was composed per liter of 45 g of maltose, 1 g of $MgSO_4.7H_2O$, 1 g of NaCl, 2 g of $K_2HSO_4$, 12 g of $KH_2PO_4$, 2 g of urea, and 500 µl of AMG trace metals, the pH was adjusted to 5.0 and then filter sterilized with a 0.22 µm filtering unit.

AMG trace metals was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, and 3 g of citric acid.

SOC medium was composed of 2% tryptone, 0.5% yeast extract, 10 mM NaCl, 2.5 mM KCl, 10 mM $MgCl_2$, and 10 mM $MgSO_4$, sterilized by autoclaving and then added filter-sterilized glucose to 20 mM.

Freezing medium was composed of 60% SOC and 40% glycerol.

2×YT medium was composed per liter of 16 g of tryptone, 10 g of yeast extract, 5 g of NaCl, and 15 g of Bacto agar, sterilize by autoclaving.

Example 1

Expressed Sequence Tags (EST) cDNA Library Construction

*Thielavia terrestris* NRRL 8126 was cultivated in 50 ml of NNCYPmod medium supplemented with 1% glucose in a 250 ml flask at 45° C., 200 rpm for 24 hours. A two ml aliquot from the 24 hour liquid culture was used to seed a 500 ml flask containing 100 ml of NNCYPmod medium supplemented with 2% Sigmacell-20 (Sigma Chemical Co., St. Louis, Mo.). The culture was incubated at 45° C., 200 rpm for 3 days. The mycelia were harvested by filtration through a Buchner funnel with a glass fiber prefilter (Nalgene, Rochester N.Y.), washed twice with 10 mM Tris-HCl-1 mM EDTA pH 8 (TE), and quick frozen in liquid nitrogen.

Total RNA was isolated using the following method. Frozen mycelia of *Thielavia terrestris* NRRL 8126 were ground in an electric coffee grinder. The ground material was mixed 1:1 v/v with 20 ml of Fenazol (Ambion, Inc., Austin, Tex.) in a 50 ml Falcon tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volumes of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate-treated water (DEPC-water).

The quality and quantity of the purified RNA was assessed with an Agilent Bioanalyzer 2100 (Agilent Technologies, Inc., Palo Alto, Calif.). Polyadenylated mRNA was isolated from 360 µg of total RNA with the aid of a Poly (A) Purist Magnetic Kit (Ambion, Inc., Austin, Tex.) according to the manufacturer's instructions.

To create the cDNA library, a CloneMiner™ Kit (Invitrogen, Carlsbad, Calif.) was employed to construct a directional library that does not require the use of restriction enzyme cloning, thereby reducing the number of chimeric clones and size bias.

To insure successful first strand synthesis of the cDNA, two reactions were performed in parallel with two different concentrations of mRNA (2.2 and 4.4 µg of poly(A)$^+$ mRNA). The mRNA samples were mixed with a Biotin-attB2-Oligo (dt) primer (CloneMiner™ Kit, Invitrogen, Carlsbad, Calif.), 1× first strand buffer (Invitrogen, Carlsbad, Calif.), 2 µl of 0.1 M dithiothreitol (DTT), 10 mM of each dNTP, and water to a final volume of 18 and 16 µl, respectively. The reaction mixtures were mixed carefully and then 2 and 4 µl of Super-Script™ reverse transcriptase (Invitrogen, Carlsbad, Calif.) were added and incubated at 45° C. for 60 minutes to synthesize the first complementary strand.

For second strand synthesis, to each first strand reaction was added 30 µl of 5× second strand buffer (Invitrogen, Carlsbad, Calif.), 3 µl of 10 mM of each dNTP, 10 units of *E. coli* DNA ligase (Invitrogen, Carlsbad, Calif.), 40 units of *E. coli* DNA polymerase I (Invitrogen, Carlsbad, Calif.), and 2 units of *E. coli* RNase H (Invitrogen, Carlsbad, Calif.) in a total volume of 150 µl. The mixtures were then incubated at 16° C. for two hours. After the two-hour incubation, 2 µl of T4 DNA polymerase (Invitrogen, Carlsbad, Calif.) were added to each reaction and incubated at 16° C. for 5 minutes to create a bunt-ended cDNA. The cDNA reactions were extracted with a mixture of phenol-chloroform-isoamyl alcohol 25:24:1 v/v/v and precipitated in the presence of 20 µg of glycogen, 120 µl of 5 M ammonium acetate, and 660 µl of ethanol. After centrifugation at 12,000×g for 30 minutes at 4° C., the cDNA pellets were washed with cold 70% ethanol, dried under vacuum for 2-3 minutes, and resuspended in 18 µl of DEPC-water. To each resuspended cDNA sample was added 10 µl of 5× adapted buffer (Invitrogen, Carlsbad, Calif.), 10 µg of attB1 adapter (Invitrogen, Carlsbad, Calif.) shown below, 7 µl of 0.1 M DTT, and 5 units of T4 DNA ligase (Invitrogen, Carlsbad, Calif.).

```
attB1 adapter top strand:
                                  (SEQ ID NO: 3)
5'-TCGTCGGGGACAACTTTGTACAAAAAAGTTGG-3' attB1 adapter bottom strand:
                                  (SEQ ID NO: 4)
3'-CCCCTGTTGAAACATGTTTTTTCAACCp-5'
```

Ligation reactions were incubated overnight at 16° C. Excess adapters were removed by size-exclusion chromatography in 1 ml of Sephacryl™ S-500 HR resin (Amersham Biosciences, Piscataway, N.J.). Column fractions were collected according to the CloneMiner™ Kit's instructions and fractions 3 to 14 were analyzed with an Agilent Bioanalyzer to determine the fraction at which the attB1 adapters started to elute. This analysis showed that the adapters started eluting around fraction 10 or 11. For the first library fractions 6 to 11 were pooled and for the second library fractions 4-11 were pooled.

Cloning of the cDNA was performed by homologous DNA recombination according to the Gateway System protocol (Invitrogen, Carlsbad, Calif.) using BP Clonase™ (Invitrogen, Carlsbad, Calif.) as the recombinase. Each BP Clonase™ recombination reaction contained approximately 70 ng of attB-flanked-cDNA, 250 ng of pDONR™222, 2 µl of 5×BP Clonase™ buffer, 2 µl of TE buffer, and 3 µl of BP Clonase™. All reagents were obtained from Invitrogen, Carlsbad, Calif. Recombination reactions were incubated at 25° C. overnight.

Heat-inactivated BP recombination reactions were then divided in 6 aliquots and electroporated into ElectroMax™ DH10B electrocompetent cells (Invitrogen, Carlsbad, Calif.) using a BioRad Gene Pulser II (BioRad, Hercules, Calif.) with the following parameters: Voltage: 2.0 kV; Resistance: 200Ω; and Capacity: 25 µF. Electroporated cells were resuspended in 1 ml of SOC medium and incubated at 37° C. for 60 minutes with constant shaking at 200 rpm. After the incubation period, the transformed cells were pooled and mixed 1:1 with freezing medium. A 200 µl aliquot was removed for library titration and then the rest of each library was aliquoted into 1.8 ml cryovials (Wheaton Science Products, Millville, N.J.) and stored frozen at −80° C.

Four serial dilutions of each library were prepared: 1/100, 1/1000, $1/10^4$, $1/10^5$. From each dilution 100 µl were plated onto 150 mm LB plates supplemented with 50 µg of kanamycin per ml and incubated at 3° C. overnight. The number of colonies on each dilution plate were counted and used to calculate the total number of transformants in each library.

The first library was shown to have 5.4 million independent clones and the second library was show to have 9 million independent clones.

Example 2

Template Preparation and Nucleotide Sequencing of cDNA Clones

Aliquots from both libraries were mixed and plated onto 25×25 cm LB plates supplemented with 50 µg of kanamycin per ml. Individual colonies were arrayed onto 96-well plates containing 100 µl of LB supplemented with 50 µg of kanamycin per ml with the aid of a Genetix QPix Robot (Genetix Inc., Boston, Mass.). Forty five 96-well plates were obtained for a total of 4320 individual clones. The plates were incubated overnight at 37° C. with shaking at 200 rpm. After incubation, 100 µl of sterile 50% glycerol was added to each well. The transformants were replicated with the aid of a 96-pin tool (Boekel, Feasterville, Pa.) into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of kanamycin per ml in each well. The primary microtiter plates were stored frozen at −80° C. The secondary deep-dish plates were incubated at 37° C. overnight with vigorous agitation at 300 rpm on a rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover. Plasmid DNA was prepared with a MWG Robot-Smart 384 (MWG Biotech Inc., High Point, N.C.) and Montage Plasmid Miniprep Kits (Millipore, Billerica, Mass.).

Sequencing reactions were performed using Big-Dye™ (Applied Biosystems, Inc., Foster City, Calif.) terminator chemistry (Giesecke et al., 1992, *Journal of Virology Methods* 38: 47-60) and a M13 Forward (−20) sequencing primer shown below.

5'-GTAAAACGACGGCCAG-3'   (SEQ ID NO: 5)

The sequencing reactions were performed in a 384-well format with a Robot-Smart 384 (MWG Biotech Inc., High Point, N.C.) and terminator removal with Millipore Multi-Screen Seq384 Sequencing Clean-up Kits (Millipore, Billerica, Mass.). Reactions contained 6 µl of plasmid DNA and 4 µl of sequencing master-mix containing 2 µl of 5× sequencing buffer (Millipore, Billerica, Mass.), 1 µl of Big-Dye™ terminator (Applied Biosystems, Inc., Foster City, Calif.), 1.6 pmoles of M13 Forward primer, and 1 µl of water. Single-pass DNA sequencing was performed with an ABI PRISM Automated DNA Sequencer Model 3700 (Applied Biosystems, Foster City, Calif.).

Example 3

Analysis of DNA Sequence Data of cDNA Clones

Base calling, quality value assignment, and vector trimming were performed with the assistance of PHRED/PHRAP software (University of Washington, Seattle, Wash.). Clustering analysis of the ESTs was performed with a Parcel Transcript Assembler v. 2.6.2. (Paracel, Inc., Pasadena, Calif.). Analysis of the EST clustering indicated 395 independent clusters.

Sequence homology analysis of the assembled EST sequences against the PIR database was performed with the Blastx program (Altschul et. al., 1990, *J. Mol. Biol.* 215: 403-410) on a 32-node Linux cluster (Paracel, Inc., Pasadena, Calif.) using the BLOSUM 62 matrix (Henikoff, 1992, *Proc. Natl. Acad. Sci. USA* 89: 10915-10919) From the 395 clusters, 246 had blast hits to known genes in public protein databases and 149 had no significant hits against these databases. Among these 246 genes, 13 had hits against well characterized homologues of glycosyl hydrolase genes.

Example 4

Identification of cDNA Clones Encoding a Family 7 Endoglucanase (CEL7F)

A cDNA clone encoding a Family 7 endoglucanase (CEL7F) was initially identified by its identity to the Family 7 endoglucanase EG-1 protein from *Trichoderma longibrachiatum* (NREF NF00756647). This analysis indicated that the two proteins were 44% identical at the protein level over a 113 amino acid (339 basepairs) stretch. After this initial identification clone Tter08C4 was retrieved from the original frozen stock plate and streaked onto a LB plate supplemented with 50 µg of kanamycin per ml. The plate was incubated overnight at 37° C. and the next day a single colony from the plate was used to inoculate 3 ml of LB supplemented with 50 µg of kanamycin per ml. The liquid culture was incubated overnight at 37° C. and plasmid DNA was prepared with a BioRobot 9600 (QIAGEN, Inc., Valencia, Calif.). Clone Tter08C4 plasmid DNA was sequenced again with Big-Dye™ terminator chemistry as described above, using the M13 forward and a Poly-T primer shown below to sequence the 3' end of the clone.

```
5'-TTTTTTTTTTTTTTTTTTTTTTVN-3'     (SEQ ID NO: 6)
```

Where V=G, A, C and N=G, A, C, T

Blastx homology analysis of the sequence information indicated that the protein encoded by clone Tter08C4 was similar to the *Trichoderma reesei* EG1 protein (NREF NF00494331). These proteins were 46% identical over a 365 amino acid stretch.

Analysis of the deduced protein sequence of clone Tter08C4 with the Interproscan program (Zdobnov and Apweiler, 2001, *Bioinformatics* 17: 847-8) showed that the gene contained the sequence signature of the Family 7 proteins. This sequence signature known as the Pfam pattern PF00840 (Bateman et. al., 2002, *Nucleic Acids Research* 30: 276-280) was found 18 amino acids from the starting amino acid methionine confirming that clone Tter08C4 encodes a Family 7 endoglucanase.

The cDNA sequence (SEQ ID NO: 1) and deduced amino acid sequence (SEQ ID NO: 2) of the *Thielavia terrestris* endoglucanase are shown in FIGS. 1A and 1B. The cDNA clone encodes a polypeptide of 336 amino acids. The % G+C content of the cDNA clone of the gene is 67.5% and of the mature protein coding region (nucleotides 55 to 1011 of SEQ ID NO: 1) is 67.5%. Using the SignalP software program (Nielsen et al., 1997, *Protein Engineering* 10:1-6), a signal peptide of 17 residues was predicted. The predicted mature protein contains 319 amino acids with a molecular mass of 33.3 kDa.

A comparative alignment of endoglucanase Family 7 sequences was determined by the Clustal W method (Higgins, 1989, supra) using the LASERGENE™ MEGA-LIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the mature *Thielavia terrestris* CEL7F gene shares 46.7% identity to the deduced amino acid sequence of the catalytic region of the *Trichoderma reesei* endoglucanase I gene (NREF NF00494331, Uniprot Q5BMS5) and 44.9% identity to the deduced amino acid sequence of the full-length *Trichoderma reesei* endoglucanase I gene (NREF NF00494331, Uniprot Q5BMS5). Analysis of the alignment of the catalytic regions of these proteins showed that the *Thielavia terrestris* CEL7F endoglucanase is missing at least three discrete sequence motifs that are conserved in all other known members of glycosyl hydrolase Family 7 from fungi. Two of these consist of more than ten amino acid residues and contain highly conserved residues that are not present in the *Thielavia terrestris* CEL7F endoglucanase.

Once the identity of clone Tter08C4 was confirmed, a 0.5 µl aliquot of plasmid DNA from this clone, designated pTter7F (FIG. 2), was transferred into a vial of *E. coli* TOP10 cells (Invitrogen, Carlsbad, Calif.), gently mixed, and incubated on ice for 10 minutes. The cells were then heat-shocked at 42° C. for 30 seconds and incubated again on ice for 2 minutes. The cells were resuspended in 250 µl of SOC medium and incubated at 37° C. for 60 minutes with constant shaking (200 rpm). After the incubation period, two 30 µl aliquots were plated onto LB plates supplemented with 50 µg of kanamycin per ml and incubated overnight at 37° C. The next day a single colony was picked and streaked onto three 1.8 ml cryovials containing about 1.5 ml of LB agarose supplemented with 50 µg of kanamycin per ml. The vials were sealed with PetriSeal™ (Diversified Biotech, Boston Mass.) and deposited with the Agricultural Research Service Patent Culture Collection, Northern Regional Research Center, 1815 University Street, Peoria, Ill., 61604, as NRRL B-30802, with a deposit date of Apr. 11, 2005.

Example 5

Construction of pAlLo2 Expression Vector

Expression vector pAlLo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). All mutagenesis steps were verified by sequencing using Big-Dye™ terminator chemistry as described. Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor™ in vitro Site-Directed Mutagenesis Kit (Promega, Madison, Wis.) according to the manufacturer's instructions using the following primers (underlined nucleotide represents the changed base):

```
AMDS3NcoMut (2050):
5'-GTGCCCCATGATACGCCTCCGG-3'        (SEQ ID NO: 7)

AMDS2NcoMut (2721):
5'-GAGTCGTATTTCCAAGGCTCCTGACC-3'    (SEQ ID NO: 8)

AMDS1NcoMut (3396):
5'-GGAGGCCATGAAGTGGACCAACGG-3'      (SEQ ID NO: 9)
```

A plasmid comprising all three expected sequence changes was then submitted to site-directed mutagenesis, using a QuickChange™ Site-Directed Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

```
Upper Primer to mutagenize the AMG terminator
sequence:
                                    (SEQ ID NO: 10)
5'-CACCGTGAAAGCCATGCTCTTTCCTTCGTGTAGAAGACCAGACAG-3'

Lower Primer to mutagenize the AMG terminator
sequence:
                                    (SEQ ID NO: 11)
5'-CTGGTCTTCTACACGAAGGAAAGAGCATGGCTTTCACGGTGTCTG-3'
```

Figure 3:
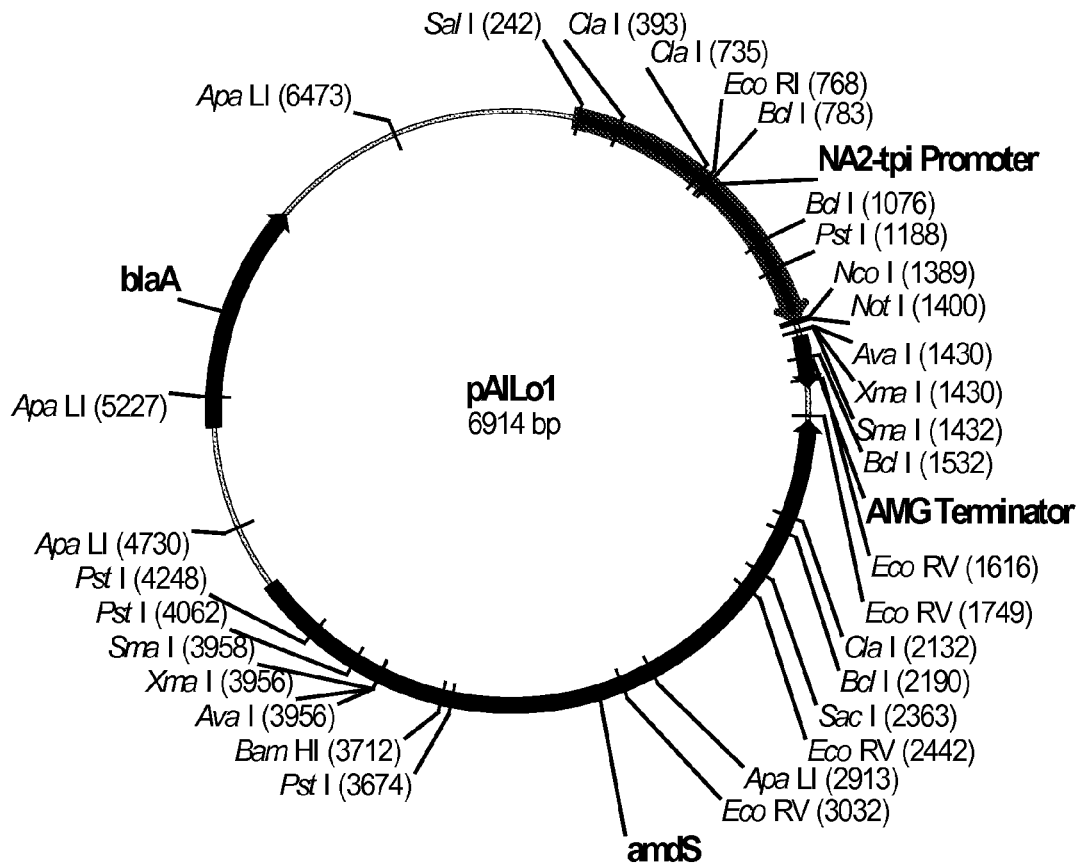
FIG. 3 shows a restriction map of pAILo1.

The last step in the modification of pBANe6 was the addition of a new Nco I restriction site at the beginning of the polylinker using a QuickChange™ Site-Directed Mutagenesis Kit and the following primers (underlined nucleotides represent the changed bases) to yield pAlLo1 (FIG. 3).

```
Upper Primer to mutagenize the NA2-tpi promoter:
                                      (SEQ ID NO: 12)
5'-CTATATACACAACTGGATTTACCATGGGCCCGCGGCCGCAGATC-3'

Lower Primer to mutagenize the NA2-tpi promoter:
                                      (SEQ ID NO: 13)
5'-GATCTGCGGCCGCGGGCCCATGGTAAATCCAGTTGTGTATATAG-3'
```

Figure 4:
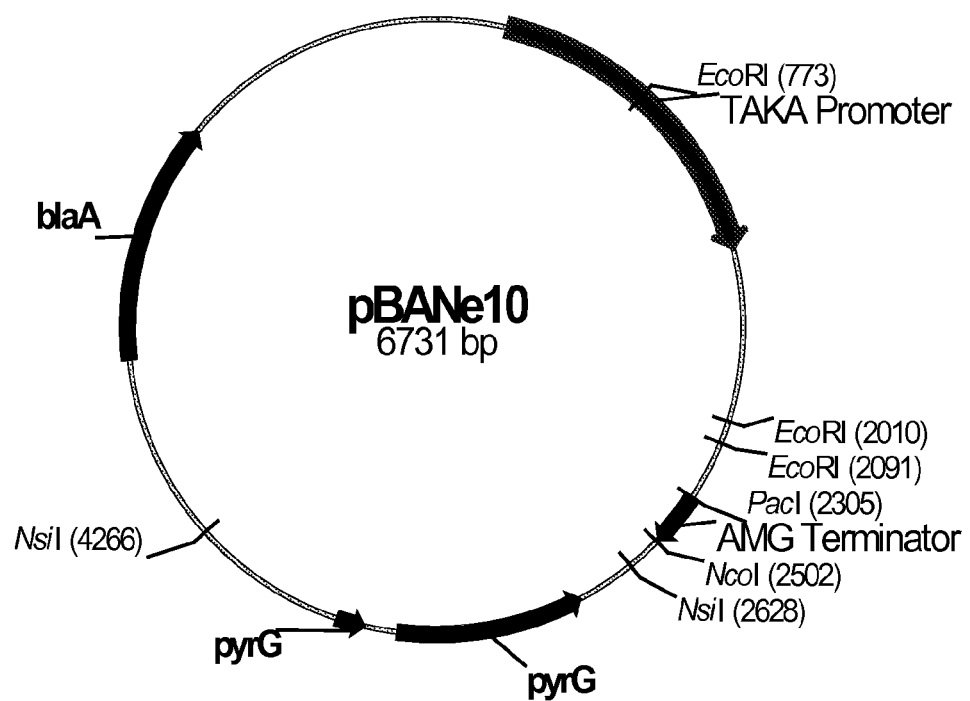
FIG. 4 shows a restriction map of pBANe10.
Figure 5:
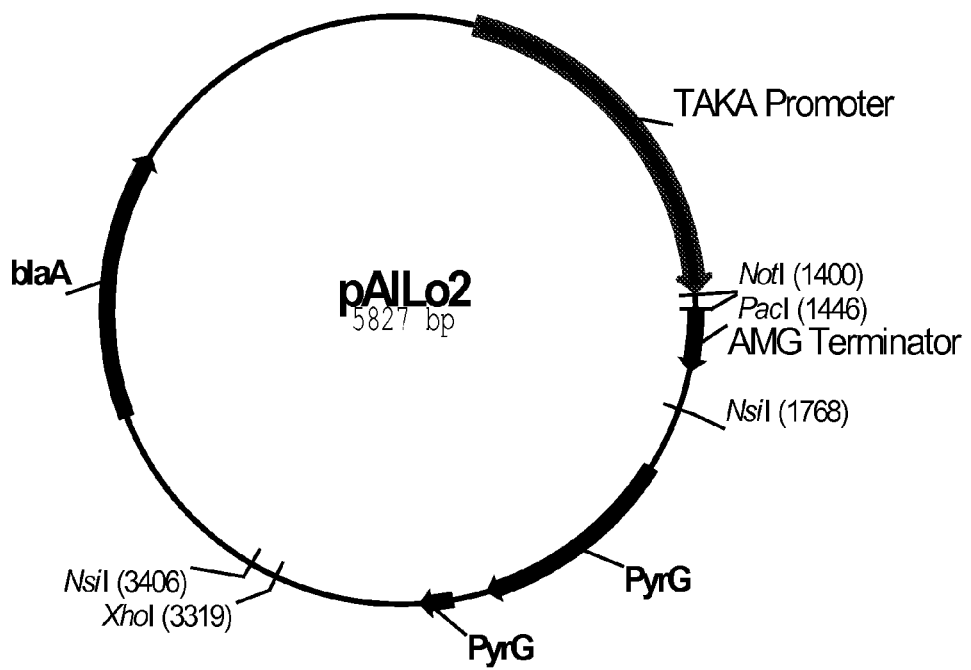
FIG. 5 shows a restriction map of pAILo2.

The amdS gene of pAlLo1 was swapped with the *Aspergillus nidulans* pyrG gene. Plasmid pBANe10 (FIG. 4) was used as a source for the pyrG gene as a selection marker. Analysis of the sequence of pBANe10 showed that the pyrG marker was contained within an Nsi I restriction fragment and does not contain either Nco I or Pac I restriction sites. Since the amdS is also flanked by Nsi I restriction sites the strategy to switch the selection marker was a simple swap of Nsi I restriction fragments. Plasmid DNA from pAlLo1 and pBANe10 were digested with the restriction enzyme Nsi I and the products purified by agarose gel electrophoresis. The Nsi I fragment from pBANe10 containing the pyrG gene was ligated to the backbone of pAlLo1 to replace the original Nsi I DNA fragment containing the amdS gene. Recombinant clones were analyzed by restriction digest to determine that they had the correct insert and also its orientation. A clone with the pyrG gene transcribed in the counterclockwise direction was selected. The new plasmid was designated pAlLo2 (FIG. 5).

Example 6

Cloning of the Family CEL7F Endoglucanase Gene into an *Aspergillus oryzae* Expression Vector Two synthetic oligonucleotide primers, shown below, were designed to PCR amplify the full-length open reading frame from *Thielavia terrestris* EST Tter08C4 encoding a Family CEL7F endoglucanase. An In-Fusion Cloning Kit (BD Biosciences, Palo Alto, Calif.) was used to clone the fragment directly into pAlLo2.

```
In-Fusion Forward primer:
                                      (SEQ ID NO: 14)
5'-ACTGGATTACCATGACCCTACGGCTCCCTGTCATCA-3'

In-Fusion Reverse primer:
                                      (SEQ ID NO: 15)
5'-TCACCTCTAGTTAATTAACTAGTTCTTCGTGGTAGACC-3'
```

Bold letters represent coding sequence. The remaining sequence contains sequence identity compared with the insertion sites of pAlLo2.

Fifty picomoles of each of the primers above were used in a PCR reaction containing 50 ng of pTter11C9 DNA, 1× Pfx Amplification Buffer (Invitrogen, Carlsbad, Calif.), 6 µl of 10 mM blend of dATP, dTTP, dGTP, and dCTP, 2.5 units of Platinum Pfx DNA Polymerase (Invitrogen, Carlsbad, Calif.), 1 µl of 50 mM MgSO$_4$, and 5 µl of 10× pCRx Enhancer solution (Invitrogen, Carlsbad, Calif.) in a final volume of 50 µl. An Eppendorf Mastercycler 5333 (Eppendorf Scientific, Inc., Westbury, N.Y.) was used to amplify the fragment programmed for one cycle at 98° C. for 2 minutes; and 35 cycles each at 94° C. for 30 seconds, 65° C. for 30 seconds, and 68° C. for 1.5 minutes. After the 35 cycles, the reaction was incubated at 68° C. for 10 minutes and then cooled at 10° C. until further processed. A 1.4 kb PCR reaction product was isolated on a 0.8% GTG-agarose gel (Cambrex Bioproducts One Meadowlands Plaza East Rutherford, N.J. 07073) using 40 mM Tris base-20 mM sodium acetate-1 mM disodium EDTA (TAE) buffer and 0.1 µg of ethidium bromide per ml. The DNA band was visualized with the aid of a Dark Reader™ (Clare Chemical Research, Dolores, Colo.) to avoid UV-induced mutations. The 1.4 kb DNA band was excised with a disposable razor blade and purified with an Ultrafree-DA spin cup (Millipore, Billerica, Mass.) according to the manufacturer's instructions.

Figure 6:
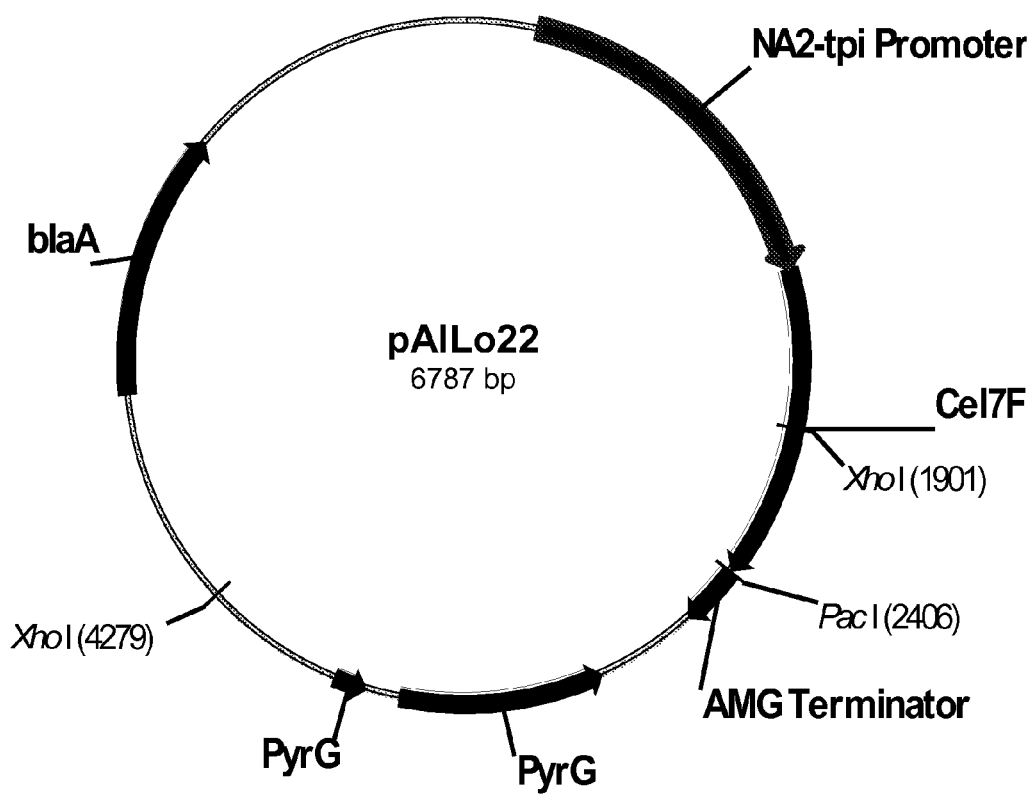
FIG. 6 shows a restriction map of pAILo22.

The vector pAlLo2 was linearized by digestion with Nco I and Pac I. The fragment was purified by gel electrophoresis and ultrafiltration as described above. Cloning of the purified PCR fragment into the linearized and purified pAlLo2 vector was performed with an In-Fusion Cloning Kit (BD Biosciences, Palo Alto, Calif.). The reaction (20 µl) contained 1× In-Fusion Buffer (BD Biosciences, Palo Alto, Calif.), 1×BSA (BD Biosciences, Palo Alto, Calif.), 1 µl of In-Fusion enzyme (diluted 1:10) (BD Biosciences, Palo Alto, Calif.), 100 ng of pAlLo2 digested with Nco I and Pac I, and 50 ng of the *Thielavia terrestris* CEL7F purified PCR product. The reaction was incubated at room temperature for 30 minutes. A 2 µl sample of the reaction was used to transform *E. coli* XL10 SoloPac® Gold cells (Stratagene, La Jolla, Calif.) according to the manufacturer's instructions. After the recovery period, two 100 µl aliquots from the transformation reaction were plated onto 150 mm 2×YT plates supplemented with 100 µg of ampicillin per ml. The plates were incubated overnight at 37° C. A set of eight putative recombinant clones was selected at random from the selection plates and plasmid DNA was prepared from each one using a BioRobot 9600. Clones were analyzed by Xho I restriction digest. Two clones that had the expected restriction digest pattern were then sequenced to confirm that there were no mutations in the cloned insert. Clone #1 was selected and designated pAlLo22 (FIG. 6).

Example 7

Expression of the *Thielavia terrestris* Family CEL7F Endoglucanase Gene in *Aspergillus oryzae* JAL250

*Aspergillus oryzae* Jal250 (WO 99/61651) protoplasts were prepared according to the method of Christensen et al., 1988, Bio/Technology 6: 1419-1422. Five micrograms of pAlLo22 (as well as pAlLo2 as a vector control) were used to transform *Aspergillus oryzae* JAL250 protoplasts.

The transformation of *Aspergillus oryzae* Jal250 with pAlLo2 yielded about 50 transformants. Eight transformants were isolated to individual PDA plates and incubated for five days at 34° C.

Confluent spore plates were washed with 5 ml of 0.01% Tween 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five µl of each supernatant were mixed with an equal volume of 2× loading buffer (10% β-mercaptoethanol) and loaded onto a 1.5 mm 8%-16% Tris-Glycine SDS-PAGE gel and stained with Simply Blue SafeStain (Invitrogen, Carlsbad, Calif.). SDS-PAGE profiles of the culture broths showed that six out of eight transformants had a new protein band of approximately 40 kDa. Transformant number 7 was selected for further studies and designated *Aspergillus oryzae* Jal250AlLo22.

Example 8

Large Shake Flask Cultures of *Aspergillus oryzae* Jal250AlLo22

*Aspergillus oryzae* Jal250AlLo22 spores were spread onto a PDA plate and incubated for five days at 34° C. The confluent spore plate was washed twice with 5 ml of 0.01% Tween 80 to maximize the number of spores collected. The spore suspension was then used to inoculate 500 ml of MDU2BP medium in a two-liter Fernbach flask. The transformant culture was incubated at 34° C. with constant shaking (200 rpm). At day five post-inoculation, the culture broth was collected by filtration on a 500 ml, 75 mm Nylon filter unit with a pore size of 0.45 µm with a glass-fiber pre-filter. A 5 µl sample of the broth was analyzed by SDS-PAGE as described above to confirm that the protein pattern was the same as the one obtained before. Once the broth was shown to contain the 40 kDa protein band, the broth was submitted to enzymatic characterization.

sealer (ALPS-300, Abgene, Epsom, UK). Eight hundred µl of the above substrates (6.25 g per liter of 50 mM sodium acetate pH 5.0) were transferred into each well of the 96-deep-well-plate, followed by 180 µl of 50 mM sodium acetate pH 5.0 and 20 µl of *Thielavia terrestris* CEL7F endoglucanase solution (0.25 g/L) to start the reactions. The substrate concentration and enzyme loading in the final reaction mixture were 5 g per liter and 1 mg of enzyme per g of substrate, respectively. *Aspergillus oryzae* Jal250 broth was tested along with *Thielavia terrestris* CEL7F endoglucanase broth under the same condition, serving as a negative control. The reactions were incubated at 50° C. without mixing. Before sampling, the deep well plates were centrifuged in a plate centrifuge (Sorvall RT7, Global Medical Instrumentation, Ramsey, Minn.) at 3000 rpm for 5 minutes. A 150 µl sample of the supernatant was transferred into a 96-well filtration plate (0.45 µm pore size, Millipore, Billerica, Mass.), vacuumed and filtrate was collected. A 100 µl sample of the filtrate was transferred into another 96-well plate and the absorbance at 590 nm was measured using a Spectra MAX340 (Molecular Devices, Sunnyvale, Calif.).

After 1 hour and 92 hour incubations, the dye released from the different dyed substrates by *Thielavia terrestris* CEL7F endoglucanase (after subtracting the dye released by *Aspergillus oryzae* Jal250) are shown in Table 1 as relative 590 nm values.

TABLE 1

Relative $A_{590\ nm}$ after incubating *Thielavia terrestris* endoglucanase with different dyed substrates for 1 hour and 92 hours at 50° C., pH 5.0.

| Time hr | AX | βG | Dex | HEC | Gal | GM | Xly | XG | Chitin Azure |
|---|---|---|---|---|---|---|---|---|---|
| 1 | 0.00 | 0.22 | 0.00 | 0.16 | 0.00 | 0.00 | 0.01 | 0.01 | 0.00 |
| 92 | 0.58 | 0.78 | 0.00 | 1.00 | 0.00 | 0.08 | 0.32 | 0.75 | 0.00 |

AX: AZCL-arabinoxylan
βG: AZCL-β-glucan
Dex: AZCL-dextran
HEC: AZCL-HE-cellulose
Gal: AZCL-patato galactan
GM: AZCL-galactomannan
Xly: AZCL-xylan
XG: AZCL-xyloglucan Example 9

Characterization of the *Thielavia terrestris* CEL7F Endoglucanase

The *Aspergillus oryzae* Jal250AlLo22 broth described in Example 8 was filtered through a 0.22 µm pore-size filter (Millipore, Billerica, Mass.), concentrated using an Amicon stirred cell equipped with a PM10 membrane (Millipore, Billerica, Mass.), and desalted using an Econo-Pac 10DG column (BioRad Laboratories, Hercules, Calif.).

Broth from *Aspergillus oryzae* Jal250 (vector alone), as a negative control, was treated the same as above.

Dyed substrates used to evaluate the substrate specificity of the *Thielavia terrestris* CEL7F endoglucanase included: AZCL-arabinoxylan (wheat), AZCL-β-glucan, AZCL-dextran, AZCL-HE-cellulose, AZCL-potato galactan, AZCL-galactomannan (Carob), AZCL-xylan (Birchwood), AZCL-xyloglucan (Megazyme, Bray, Ireland), and Chitin Azure (Sigma, St Louis, Mo.).

The activity assays were performed in 96-deep-well plates (Axygen Scientific, Union City, Calif.) sealed by a plate

*Thielavia terrestris* CEL7F endoglucanase possessed activity toward AZCL-β-glucan and AZCL-HE-cellulose after 1 hour. *Thielavia. terrestris* CEL7F endoglucanase also showed activity on the arabinoxylan, xylan, and xyloglucan dyed substrates, and low activity on the galactomannan dyed substrate after a 92 hour incubation.

Example 10

Hydrolysis of Pretreated Corn Stover with the *Thielavia terrestris* CEL7F Endoglucanase Corn stover was pretreated at the U.S. Department of Energy National Renewable Energy Laboratory (NREL) using dilute sulfuric acid. The following conditions were used for the pretreatment: 0.048 g sulfuric acid/g dry biomass at 190° C. and 25% w/w dry solids for around 1 minute. The water-insoluble solids in the pretreated corn stover (PCS) contained 52% cellulose, 3.6% hemicellulose, and 29.8% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003. Prior to enzymatic hydrolysis, the PCS was washed with a large volume of double distilled water until the pH was higher than 4.0, and was then sieved through a 100-mash sieve and autoclaved at 121° C. for 30 minutes.

Hydrolysis of PCS was conducted in 96-deep-well plates, (Axygen Scientific, Union City, Calif.) sealed by a plate sealer (ALPS-300, Abgene, Epsom, UK), with a total reaction volume of 1.0 ml. Hydrolysis of PCS (10 mg/ml in 50 mM sodium acetate pH 5.0 buffer) was performed using 1.25 mg of *Thielavia terrestris* CEL7F endoglucanase (prepared as described in Example 9) per gram of PCS. Broth from *Aspergillus oryzae* Jal250 (prepared as described in Example 9) was run as a control. PCS hydrolysis was performed at 50° C., pH 5.0. Reactions were run in duplicates and aliquots were taken during the course of hydrolysis. PCS hydrolysis reactions were stopped by mixing a 20 µl aliquot of each hydrolyzate with 180 µl of 0.11 M NaOH (stop reagent). Appropriate serial dilutions were generated for each sample and the reducing sugar content determined using a para-hydroxybenzoic acid hydrazide (PHBAH, Sigma, St. Louis, Mo.) assay adapted to a 96 well microplate format as described below. Briefly, a 90 µl aliquot of an appropriately diluted sample was placed in a 96 well conical bottomed microplate. Reactions were initiated by adding 60 µl of 1.5% (w/v) PHBAH in 2% NaOH to each well. Plates were heated uncovered at 95° C. for 10 minutes. Plates were allowed to cool to room temperature (RT) and 50 µl of distilled $H_2O$ added to each well. A 100 µl aliquot from each well was transferred to a flat bottomed 96 well plate and the absorbance at $A_{410nm}$ measured using a SpectraMax Microplate Reader (Molecular Devices, Sunnyvale, Calif.). Glucose standards (0.1-0.0125 mg/ml diluted with 0.4% sodium hydroxide) were used to prepare a standard curve to translate the obtained $A_{410nm}$ values into glucose equivalents. The resultant equivalents were used to calculate the percentage of PCS cellulose conversion for each reaction. The degree of cellulose conversion to reducing sugar (conversion, %) was calculated using the following equation:

$$\text{Conversion}_{(\%)} = RS_{(mg/ml)} * 100 * 162 / (Cellulose_{(mg/ml)} * 180)$$

$$= RS_{(mg/ml)} * 100 / (Cellulose_{(mg/ml)} * 1.111)$$

In this equation, RS is the concentration of reducing sugar in solution measured in glucose equivalents (mg/ml), and the factor 1.111 reflects the weight gain in converting cellulose to glucose.

PCS hydrolysis by the *Thielavia terrestris* CEL7F endoglucanase (1.25 mg/g PCS) yielded a cellulose conversion of 2.1% after 120 hours. *Aspergillus oryzae* Jal250 (1.25 mg/g PCS) yielded less than 1% conversion after 120 hours.

Example 11

Hydrolysis of Soluble Beta-Glucan from Barley by *Thielavia terrestris* Endoglucanase The *Thielavia terrestris* Cel7F endoglucanase was tested in the form of the *Aspergillus oryzae* Jal250AlLo22 broth described in Example 8. The broth was concentrated and exchanged to 50 mM sodium acetate pH 5.0 using Centricon Plus-20 centrifugal filter with Biomax-5 polyethersulfone membrane (5000 NMWL) from Millipore (Bedford, Mass.). Broth from *Aspergillus oryzae* Jal250 (vector alone) was treated the same as above.

The protein concentration in the enzyme solutions was determined using the Bicinchoninic Acid (BCA) microplate assay according to the manufacturer's instructions for a BCA Protein Assay Reagent Kit (Pierce Chemical Co., Rockford, Ill.).

Enzyme dilutions were prepared fresh before each experiment from stock enzyme solutions, which were stored at −20° C.

The activity of the *Thielavia terrestris* Cel7F endoglucanase on soluble beta-glucan from barley (medium viscosity, 230 kDa, Megazyme International Ireland Ltd., Bray, Ireland) was determined at pH 5.5 (50 mM sodium acetate with 0.02% sodium azide) and 60° C. The results were compared with those for *Trichoderma reesei* Cel7B (EGI) endoglucanase. Recombinant *Trichoderma reesei* Cel7B (EGI) endoglucanase can be prepared according to Takashima et al., 1998, *Journal of Biotechnology* 65: 163-171.

The initial concentration of beta-glucan in the hydrolysis reactions was 1.0% (w/v). One ml reactions were run without stirring in Eppendorf 96 DeepWell Plates (1.2 ml, VWR Scientific, West Chester, Pa.). The enzymes were used at three protein loadings, 0.05, 0.1, and 0.2 mg per g of glucan. In control reactions, the endoglucanases were substituted with 50 mM sodium acetate pH 5.5 containing 0.02% sodium azide (buffer control) or with concentrated and buffer exchanged *Aspergillus oryzae* Jal250 broth containing no recombinantly expressed enzymes (Jal250 control).

Figure 7:
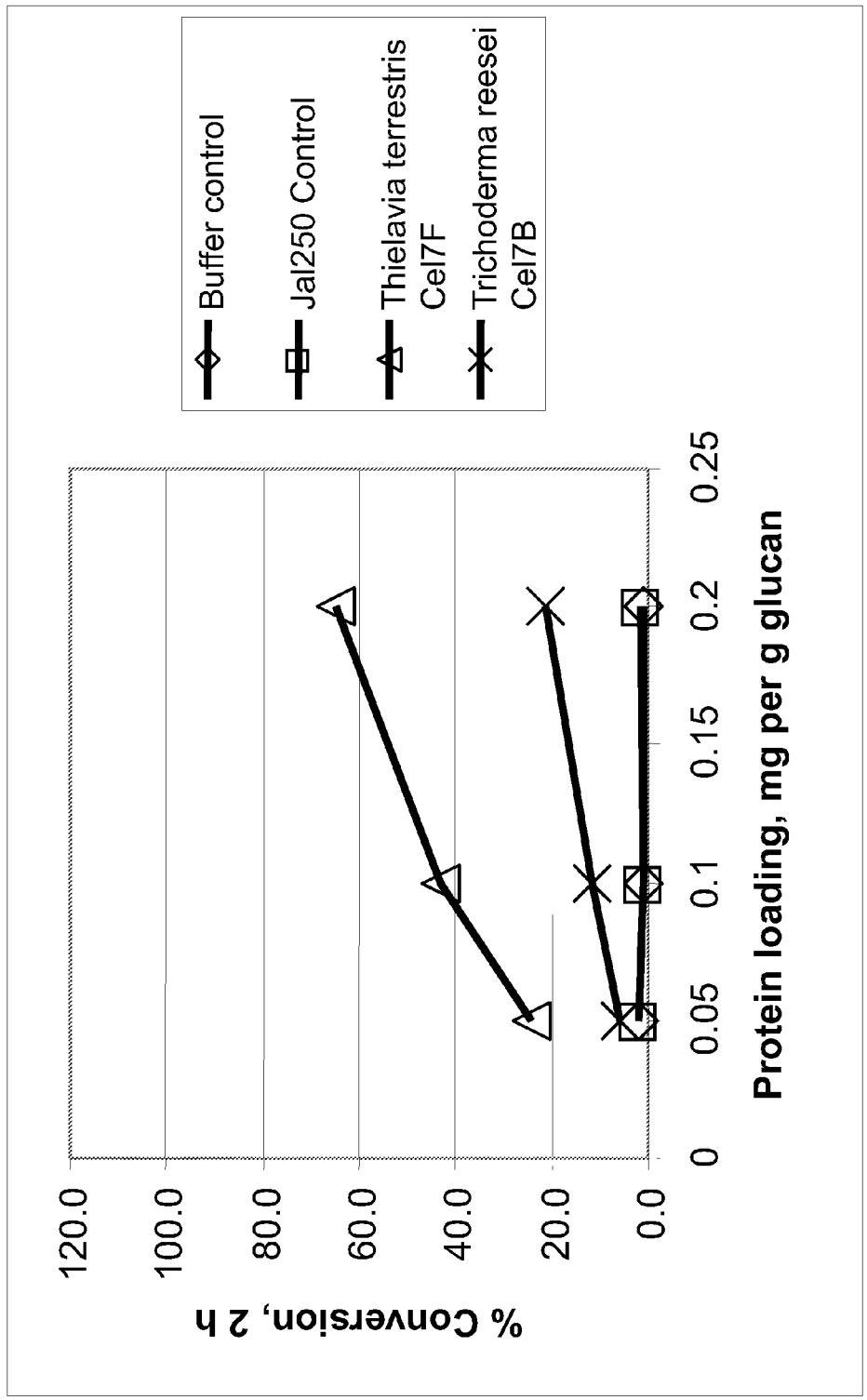
FIG. 7 shows the relative conversion of beta-glucan (1% w/v) after 2 hours of hydrolysis at pH 5.5 and 60° C.
Figure 8:
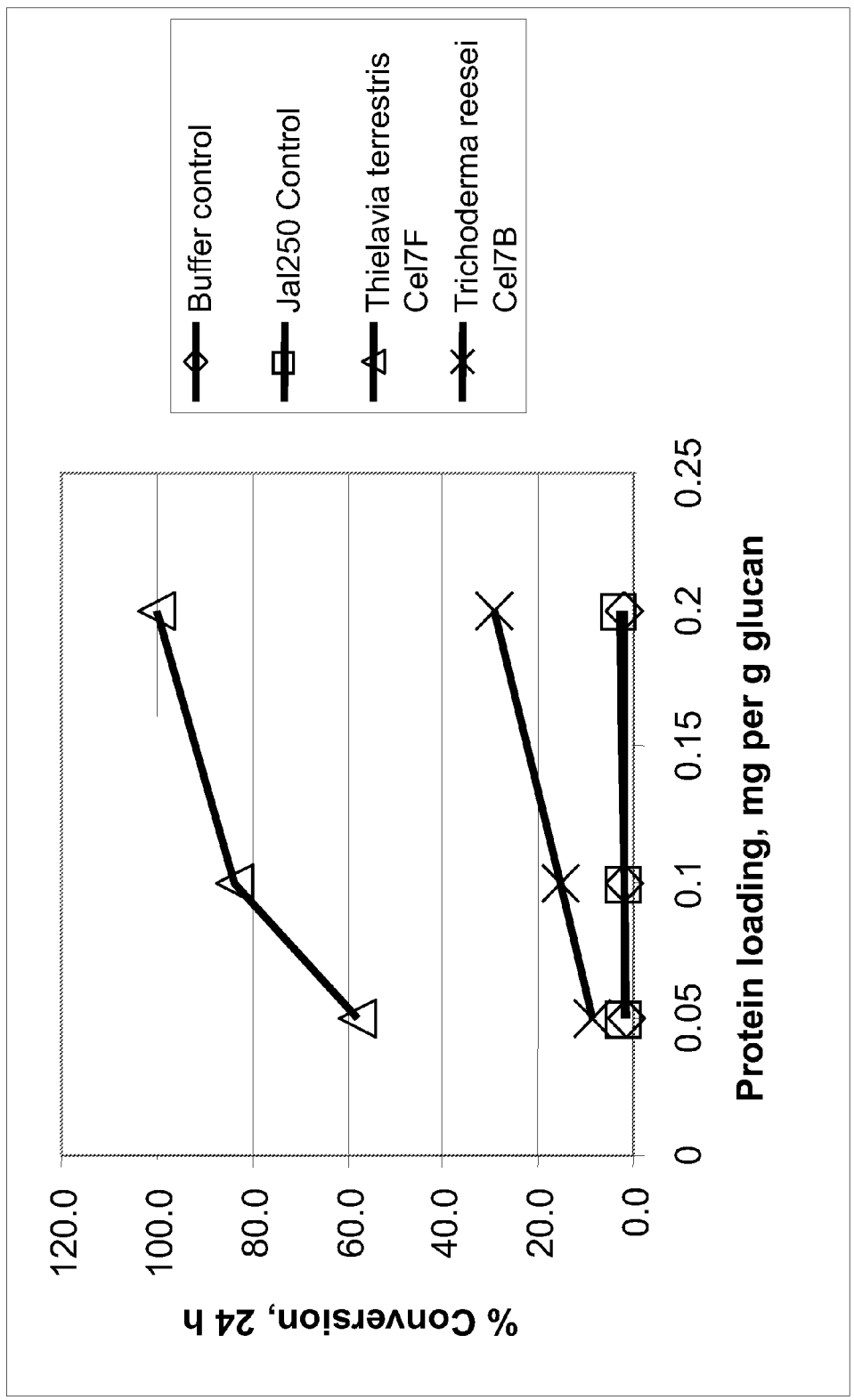
FIG. 8 shows the relative conversion of beta-glucan (1% w/v) after 24 hours of hydrolysis at pH 5.5 and 60° C.

Aliquots were removed from the hydrolysis reactions at 2 hours and 24 hours, diluted with deionized water, and analyzed for reducing sugars using the p-hydroxybenzoic acid hydrazide (PHBAH) assay as described in Example 10. The relative conversion of beta-glucan as a function of protein loading at two incubation times, 2 hours and 24 hours, is shown in FIGS. 7 and 8, respectively. The relative conversion is shown as a percentage of conversion obtained after 24-hour hydrolysis of beta-glucan by *Thielavia terrestris* Cel7F endoglucanase (0.2 mg protein per g of glucan).

The *Thielavia terrestris* Cel7F endoglucanase showed higher conversion of beta-glucan than the *Trichoderma reesei* Cel7B endoglucanase and continued to produce new reducing end-groups beyond the 2 hour incubation time. In contrast, the *Trichoderma reesei* Cel7B endoglucanase showed almost no additional increase in reducing sugar concentration after 2 hours of hydrolysis.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* pTter7F | NRRL B-30837 | Apr. 11, 2005 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polynucleotide encoding a polypeptide having endoglucanase activity, selected from the group consisting of:
   (a) a polynucleotide encoding a polypeptide having endoglucanase activity comprising an amino acid sequence having at least 95% sequence identity with the mature polypeptide of SEQ ID NO: 2;
   (b) a polynucleotide encoding a polypeptide having endoglucanase activity which hybridizes under high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); and
   (c) a polynucleotide encoding a polypeptide having endoglucanase activity comprising a nucleotide sequence having at least 95% identity with the mature polypeptide coding sequence of SEQ ID NO: 1.

2. The isolated polynucleotide of claim 1, which encodes a polypeptide comprising an amino acid sequence having at least 95% sequence identity with the mature polypeptide of SEQ ID NO: 2.

3. The isolated polynucleotide of claim 2, which encodes a polypeptide comprising an amino acid sequence having at least 97% sequence identity with the mature polypeptide of SEQ ID NO: 2.

4. The isolated polynucleotide of claim 1, which encodes a polypeptide comprising or consisting of the amino acid sequence of SEQ ID NO: 2.

5. The isolated polynucleotide of claim 1, which encodes a polypeptide comprising or consisting of the mature polypeptide of SEQ ID NO: 2.

6. The isolated polynucleotide of claim 1, which hybridizes under high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii).

7. The isolated polynucleotide of claim 6, which hybridizes under very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii).

8. The isolated polynucleotide of claim 1, which comprises a nucleotide sequence having at least 95% sequence identity with the mature polypeptide coding sequence of SEQ ID NO: 1.

9. The isolated polynucleotide of claim 8, which comprises a nucleotide sequence having at least 97% sequence identity with the mature polypeptide coding sequence of SEQ ID NO: 1.

10. The isolated polynucleotide of claim 1, which is contained in plasmid pTter7F which is contained in E. coli NRRL B-30837.

11. A nucleic acid construct comprising the polynucleotide of claim 1 operably linked to one or more control sequences that direct the production of the polypeptide in an expression host.

12. A recombinant expression vector comprising the polynucleotide of claim 1.

13. A recombinant host cell comprising the polynucleotide of claim 1.

14. A method for producing the polypeptide having endoglucanase activity, comprising: (a) cultivating the host cell of claim 13 under conditions conducive for production of the polypeptide; and (b) recovering the polypeptide.

15. A method for producing a mutant of a parent cell, which comprises disrupting or deleting the polynucleotide of claim 1, which results in the mutant producing less of the polypeptide having endoglucanase activity than the parent cell.

16. A nucleic acid construct comprising a gene encoding a protein operably linked to a nucleotide sequence encoding a signal peptide comprising or consisting of amino acids 1 to 17 of SEQ ID NO: 2, wherein the gene is foreign to the nucleotide sequence.

17. A recombinant expression vector comprising the nucleic acid construct of claim 16.

18. A recombinant host cell comprising the nucleic acid construct of claim 16.

19. A method for producing a protein comprising: (a) cultivating the recombinant host cell of claim 18 under conditions conducive for production of the protein; and (b) recovering the protein.

20. The isolated polynucleotide of claim 1, which encodes a polypeptide comprising an amino acid sequence having at least 98% sequence identity with the mature polypeptide of SEQ ID NO: 2.

21. The isolated polynucleotide of claim 1, which encodes a polypeptide comprising an amino acid sequence having at least 99% sequence identity with the mature polypeptide of SEQ ID NO: 2.

22. The isolated polynucleotide of claim 1, which comprises a nucleotide sequence having at least 98% sequence identity with the mature polypeptide coding sequence of SEQ ID NO: 1.

23. The isolated polynucleotide of claim 1, which comprises a nucleotide sequence having at least 99% sequence identity with the mature polypeptide coding sequence of SEQ ID NO: 1.

24. The isolated polynucleotide of claim 1, wherein the mature polypeptide is amino acids 18 to 336 of SEQ ID NO: 2.

25. The isolated polynucleotide of claim 1, wherein the mature polypeptide coding sequence is nucleotides 52 to 1008 of SEQ ID NO: 1.

* * * * *

SEQUENCE LISTING

<160> NUMBER OF SEQ ID NOS: 15

<210> SEQ ID NO 1
<211> LENGTH: 1011
<212> TYPE: DNA
<213> ORGANISM: Thielavia terrestris

<400> SEQUENCE: 1

```
atgaccctac ggctccctgt catcagcctg ctggcctcgc tggcagcagg cgccgtcgtc      60
gtcccacggg cggagtttca ccccctctc ccgacttgga aatgcacgac ctccggggc     120 tgcgtgcagc agaacaccag cgtcgtcctg gaccgtgact cgaagtacgc cgcacacagc     180
gccggctcgc ggacggaatc ggattacgcg gcaatgggag tgtccacttc gggcaatgcc     240
gtgacgctgt accactacgt caagaccaac ggcaccctcg tccccgcttc gccgcgcatc     300
tacctcctgg gcgcggacgg caagtacgtg cttatggacc tcctcaacca ggagctgtcg     360
gtggacgtcg acttctcggc gctgccgtgc ggcgagaacg gggccttcta cctgtccgag     420 atggcggcg acgggcgggg cgacgcgggg gcgggcgacg ggtactgcga cgcgcagtgc     480
cagggctact gctgcaacga gatggacatc ctcgaggcca actcgatggc gacggccatg     540
acgccgcacc cgtgcaaggg caacaactgc gaccgcagcg gctgcggcta caacccgtac     600
gccagcggcc agcgcggctt ctacgggccc ggcaagacgg tcgacacgag caagcccttc     660
accgtcgtca cgcagttcgc cgccagcggc ggcaagctga cccagatcac ccgcaagtac     720
atccagaacg gccgggagat cggcggcggc ggcaccatct ccagctgcgg ctccgagtct     780
tcgacgggcg gcctgaccgg catgggcgag gcgctggggc gcggaatggt gctggccatg     840
agcatctgga acgacgcggc ccaggagatg gcatggctcg atgccggcaa caacggccct     900
tgcgccagtg gccagggcag cccgtccgtc attcagtcgc agcatcccga cacccacgtc     960
gtcttctcca acatcaggtg gggcgacatc gggtctacca cgaagaacta g            1011
```

<210> SEQ ID NO 2
<211> LENGTH: 336
<212> TYPE: PRT
<213> ORGANISM: Thielavia terrestris

<400> SEQUENCE: 2

```
Met Thr Leu Arg Leu Pro Val Ile Ser Leu Leu Ala Ser Leu Ala Ala
1               5                   10                  15

Gly Ala Val Val Val Pro Arg Ala Glu Phe His Pro Pro Leu Pro Thr
            20                  25                  30

Trp Lys Cys Thr Thr Ser Gly Gly Cys Val Gln Gln Asn Thr Ser Val
        35                  40                  45

Val Leu Asp Arg Asp Ser Lys Tyr Ala Ala His Ser Ala Gly Ser Arg
    50                  55                  60

Thr Glu Ser Asp Tyr Ala Ala Met Gly Val Ser Thr Ser Gly Asn Ala
```

```
                65                  70                  75                  80
            Val Thr Leu Tyr His Tyr Val Lys Thr Asn Gly Thr Leu Val Pro Ala
                            85                  90                  95
            Ser Pro Arg Ile Tyr Leu Leu Gly Ala Asp Gly Lys Tyr Val Leu Met
                           100                 105                 110
            Asp Leu Leu Asn Gln Glu Leu Ser Val Asp Val Asp Phe Ser Ala Leu
                           115                 120                 125
            Pro Cys Gly Glu Asn Gly Ala Phe Tyr Leu Ser Glu Met Ala Ala Asp
                           130                 135                 140
            Gly Arg Gly Asp Ala Gly Ala Gly Asp Gly Tyr Cys Asp Ala Gln Cys
            145                 150                 155                 160
            Gln Gly Tyr Cys Cys Asn Glu Met Asp Ile Leu Glu Ala Asn Ser Met
                               165                 170                 175
            Ala Thr Ala Met Thr Pro His Pro Cys Lys Gly Asn Asn Cys Asp Arg
                           180                 185                 190
            Ser Gly Cys Gly Tyr Asn Pro Tyr Ala Ser Gly Gln Arg Gly Phe Tyr
                           195                 200                 205
            Gly Pro Gly Lys Thr Val Asp Thr Ser Lys Pro Phe Thr Val Val Thr
                           210                 215                 220
            Gln Phe Ala Ala Ser Gly Gly Lys Leu Thr Gln Ile Thr Arg Lys Tyr
            225                 230                 235                 240
            Ile Gln Asn Gly Arg Glu Ile Gly Gly Gly Thr Ile Ser Ser Cys
                               245                 250                 255
            Gly Ser Glu Ser Ser Thr Gly Gly Leu Thr Gly Met Gly Glu Ala Leu
                           260                 265                 270
            Gly Arg Gly Met Val Leu Ala Met Ser Ile Trp Asn Asp Ala Ala Gln
                           275                 280                 285
            Glu Met Ala Trp Leu Asp Ala Gly Asn Asn Gly Pro Cys Ala Ser Gly
                           290                 295                 300
            Gln Gly Ser Pro Ser Val Ile Gln Ser Gln His Pro Asp Thr His Val
            305                 310                 315                 320
            Val Phe Ser Asn Ile Arg Trp Gly Asp Ile Gly Ser Thr Thr Lys Asn
                               325                 330                 335

<210> SEQ ID NO 3
<211> LENGTH: 32
<212> TYPE: DNA
<213> ORGANISM: Escherichia coli

<400> SEQUENCE: 3
tcgtcgggga caactttgta caaaaaagtt gg                                      32

<210> SEQ ID NO 4
<211> LENGTH: 27
<212> TYPE: DNA
<213> ORGANISM: Escherichia coli

<400> SEQUENCE: 4
cccctgttga aacatgtttt ttcaacc                                            27

<210> SEQ ID NO 5
<211> LENGTH: 16
<212> TYPE: DNA
<213> ORGANISM: Escherichia coli

<400> SEQUENCE: 5
gtaaaacgac ggccag                                                        16
```

```
<210> SEQ ID NO 6
<211> LENGTH: 25
<212> TYPE: DNA
<213> ORGANISM: Escherichia coli
<220> FEATURE:
<221> NAME/KEY: misc_feature
<222> LOCATION: (25)..(25)
<223> OTHER INFORMATION: N = A, C, G, OR T

<400> SEQUENCE: 6 ttttttttttt tttttttttt tttvn                                            25

<210> SEQ ID NO 7
<211> LENGTH: 22
<212> TYPE: DNA
<213> ORGANISM: Aspergillus nidulans

<400> SEQUENCE: 7
gtgccccatg atacgcctcc gg                                                22

<210> SEQ ID NO 8
<211> LENGTH: 26
<212> TYPE: DNA
<213> ORGANISM: Aspergillus nidulans

<400> SEQUENCE: 8
gagtcgtatt tccaaggctc ctgacc                                            26

<210> SEQ ID NO 9
<211> LENGTH: 24
<212> TYPE: DNA
<213> ORGANISM: Aspergillus nidulans

<400> SEQUENCE: 9
ggaggccatg aagtggacca acgg                                              24

<210> SEQ ID NO 10
<211> LENGTH: 45
<212> TYPE: DNA
<213> ORGANISM: Aspergillus niger

<400> SEQUENCE: 10
caccgtgaaa gccatgctct ttccttcgtg tagaagacca gacag                       45

<210> SEQ ID NO 11
<211> LENGTH: 45
<212> TYPE: DNA
<213> ORGANISM: Aspergillus niger

<400> SEQUENCE: 11
ctggtcttct acacgaagga aagagcatgg ctttcacggt gtctg                       45

<210> SEQ ID NO 12
<211> LENGTH: 44
<212> TYPE: DNA
<213> ORGANISM: Aspergillus niger

<400> SEQUENCE: 12
ctatatacac aactggattt accatgggcc cgcggccgca gatc                        44

<210> SEQ ID NO 13
<211> LENGTH: 44
<212> TYPE: DNA
<213> ORGANISM: Aspergillus niger
```

```
<400> SEQUENCE: 13
gatctgcggc cgcgggccca tggtaaatcc agttgtgtat atag                44

<210> SEQ ID NO 14
<211> LENGTH: 36
<212> TYPE: DNA
<213> ORGANISM: Thielavia terrestris

<400> SEQUENCE: 14
actggattac catgaccta cggctccctg tcatca                         36

<210> SEQ ID NO 15
<211> LENGTH: 38
<212> TYPE: DNA
<213> ORGANISM: Thielavia terrestris

<400> SEQUENCE: 15
tcacctctag ttaattaact agttcttcgt ggtagacc                      38
```